US00PP13012P2

(12) United States Plant Patent
Westhoff

(10) Patent No.: US PP13,012 P2
(45) Date of Patent: Sep. 24, 2002

(54) PETUNIA PLANT NAMED 'WESPELILA'

(75) Inventor: Heinrich Westhoff, Südlohn-Oeding (DE)

(73) Assignee: Josef + Heinrich Westhoff Gartenbau-Spezialkulturen, Sudlohn-Oeding (DE)

( * ) Notice: Subject to any disclaimer, the term of this patent is extended or adjusted under 35 U.S.C. 154(b) by 2 days.

(21) Appl. No.: 09/887,106

(22) Filed: Jun. 25, 2001

(51) Int. Cl.[7] ..... A01H 5/00
(52) U.S. Cl. ..... Plt./356
(58) Field of Search ..... Plt./356

(56) References Cited

PUBLICATIONS

UPOV–ROM GTITM Computer Database 2001/01, Feb. 6, 2001, GTI Jouve Retrieval Software, Citation for 'Wespelila'.*

* cited by examiner

*Primary Examiner*—Bruce R. Campell
*Assistant Examiner*—Annette Para
(74) *Attorney, Agent, or Firm*—C. A. Whealy

(57) ABSTRACT

A distinct cultivar of Petunia plant named 'Wespelila', characterized by its cascading and rounded plant habit; freely branching habit; short internodes, dense and bushy growth habit; large purple-colored flowers with undulating petal margins; and pleasantly fragrant flowers.

1 Drawing Sheet

BOTANICAL CLASSIFICATION

*Petunia×hybrida* cultivar Wespelila.

BACKGROUND OF THE INVENTION

The present Invention relates to a new and distinct cultivar of Petunia plant, botanically known as *Petunia×hybrida*, and hereinafter referred to by the name 'Wespelila'.

The new Petunia is a product of a planned breeding program conducted by the Inventor in Sudlohn-Oeding, Germany. The new Petunia originated from a cross made by the Inventor of a proprietary Petunia selection identifed as P9713, not patented, as the female, or seed, parent with a proprietary Petunia selection identified as P9712, not patented, as the male, or pollen, parent. The new Petunia was selected by the Inventor in 1998 in a controlled environment in Sudlohn-Oeding, Germany. Plants of the new Petunia differ primarily from plants of the parent selections in flower color.

Asexual reproduction of the new cultivar by terminal cuttings taken in Sudlohn-Oeding, Germany since 1999, has shown that the unique features of this new Petunia are stable and reproduced true to type in successive generations.

SUMMARY OF THE INVENTION

Plants of the cultivar Wespelila have not been observed under all possible environmental conditions. The phenotype may vary somewhat with variations in environment such as temperature, light intensity, daylength, water status, and fertilizer rate and level without, however, any variance in genotype.

The following traits have been repeatedly observed and are determined to be the unique characteristics of 'Wespelila'. These characteristics in combination distinguish 'Wespelila' as a new and distinct cultivar:

1. Cascading and rounded plant habit.
2. Freely branching habit.
3. Short internodes, dense and bushy growth habit.

4. Large purple-colored flowers with undulating petal margins.
5. Pleasantly fragrant flowers.

Plants of the cultivar Wespelila can be compared to plants of the Petunia cultivar Surfinia Revolution, not patented. However in side-by-side comparisons conducted by the Inventor in Sudlohn-Oeding, Germany, plants of the new Petunia and the cultivar Surfinia Revolution differ in the following characteristics:

1. Plants of the new Petunia have larger leaves than plants of the cultivar Surfinia Revolution.
2. Plants of the new Petunia have larger flowers than plants of the cultivar Surfinia Revolution.
3. Flower petals of plants of the new Petunia have a more undulating margin than flower petals of plants of the cultivar Surfinia Revolution.
4. Plants of the new Petunia have darker purple flowers than plants of the cultivar Surfinia Revolution.
5. Flowers of plants of the new Petunia are fragrant whereas flowers of plants of the cultivar Surfinia Revolution are not fragrant.

Plants of the cultivar Wespelila can be compared to plants of the Petunia cultivar Sylvana Gloria, not patented. However in side-by-side comparisons conducted by the Inventor in Sudlohn-Oeding, Germany, plants of the new Petunia and the cultivar Sylvana Gloria differ in the following characteristics:

1. Plants of the new Petunia have larger leaves than plants of the cultivar Sylvana Gloria.
2. Plants of the new Petunia have shorter internodes than plants of the cultivar Sylvana Gloria.
3. Plants of the new Petunia have larger flowers than plants of the cultivar Sylvana Gloria.
4. Plants of the new Petunia have darker purple flowers than plants of the cultivar Surfinia Revolution.
5. Flowers of plants of the new Petunia are fragrant whereas flowers of plants of the cultivar Surfinia Revolution are not fragrant.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical plant of 'Wespelila'.

The photograph at the bottom of the sheet comprises a close-up view of typical flowers and leaves of 'Wespelila'.

DETAILED BOTANICAL DESCRIPTION

In the following description, color references are made to The Royal Horticultural Society Colour Chart except where general terms of ordinary dictionary significance are used. Plants used for the photographs and the description were grown in 12-cm containers for about 10 to 12 weeks in a glass-covered greenhouse and under conditions which closely approximate commercial production conditions in Sudlohn-Oeding, Germany.

Botanical classification: *Petunia×hybrida* cultivar Wespelila.

Parentage:

*Female parent.*—*Petunia×hybrida* selection identified as P9713, not patented.

*Male parent.*—*Petunia×hybrida* selection identified as P9712, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Numerous, fine, fibrous and well-branched.

Plant description:

*Form.*—Annual flowering plant; initially upright, then cascading and rounded; plants eventually becoming spherical in shape. Viscid, glandular pubescent. Freely continuous basal branching with lateral branches potentially forming at every node.

*Usage.*—Appropriate for hanging baskets, window boxes and patio containers.

*Crop time.*—About 10 to 12 weeks after planting are required to produce finished flowering plants in 12-cm containers.

*Plant height* (*from soil level to top of plant plane*).—About 14 cm.

*Plant diameter.*—About 25 to 40 cm.

*Plant length* (*from soil level to lateral branches apices*).—About 120 to 140 cm.

*Vigor.*—Vigorous.

*Stem description.*—Main branches, length: About 90 to 110 cm. Main branches, diameter: About 4.6 mm. Lateral branches, length: About 40 to 65 cm. Lateral branches, diameter: About 2.4 mm. Internode length: Very short, about 2.4 cm. Texture: Moderate to dense, white, viscid and glandular pubescence. Color: 144B.

*Foliage description.*—Leaves simple, alternate; generally symmetrical, sessile, and long persisting. Length: About 6.2 cm. Width: About 5.1 cm. Shape: Rounded to slightly ovate. Apex: Obtuse. Base: Attenuate. Margin: Entire. Aspect: Slightly cupped. Texture, upper and lower surfaces: Slightly pubescent; blistered. Venation pattern: Pinnate. Color: Young and mature foliage, upper surface: 146A; venation, 146B. Young and mature foliage, lower surface: 146B; venation, 146C.

Flower description:

*Flower type and habit.*—Large salverform flowers; flowers face outwardly; single, axillary. Flowers persistent. Freely flowering.

*Natural flowering season.*—Long day responsive; flowering from April until frost in the autumn in Germany; flowering continuous during this period.

*Fragrance.*—Fragrant; sweet, pleasant.

*Flower longevity on the plant.*—About one week.

*Flower size.*—Diameter: About 8.2 cm. Depth (height): About 3.8 cm. Tube length: About 2.7 cm. Throat diameter, distal end: About 1.5 cm. Tube diameter, proximal end: About 7 mm.

*Flower buds.*—Length: About 3.7 cm. Diameter: About 6.5 mm. Shape: Oblong. Color: Towards apex, 86D, becoming 83B with subsequent development; towards base, 183B, becoming 83A with subsequent development.

*Petals.*—Arrangement/appearance: Single whorl of five petals, fused into flared trumpet. Length from throat: About 4 cm. Width: About 3.9 cm. Shape: Roughly spatulate. Apex: Mostly rounded with emargination. Margin: Entire, slightly undulate. Texture: Smooth, satiny. Color: When opening, upper surface: 86A. When opening, lower surface: 86C. Fully opened, upper surface: 86B, color fading to 86C to 86D with subsequent development. Fully opened, lower surface: 86D. Flower throat (inside): 79A. Flower tube (outside): 79C. Venation, upper surface: 83A. Venation, lower surface: 79D.

*Sepals.*—Arrangement/appearance: Single whorl of five sepals, fused at base; star-shaped. Length: About 1.9 cm. Width: About 7.5 mm. Shape: Oblanceolate. Apex: Rounded. Margin: Entire, undulate. Texture, upper and lower surfaces: Velvety. Color: Upper surface: 146B. Lower surface: 146C.

*Peduncles.*—Length: About 3.5 cm. Width: About 1.5 mm. Strength: Flexible and wiry, holding flowers outwardly. Texture: Pubescent. Color: 146C.

*Reproductive organs.*—Stamens: Quantity: Five per flower. Anther shape: Four-parted, reniform. Anther length: About 3 mm. Anther color: 86D. Pollen amount: Moderate. Pollen color: 91B. Pistils: Quantity: One per flower. Pistil length: About 2.2 cm. Stigma shape: Round. Stigma color: 144A. Style length: About 1.6 cm. Style color: 146D. Ovary color: 145A.

*Seed.*—Seed production has not been observed.

Disease resistance: Plants of the new Petunia have not been noted to be resistant to pathogens common to Petunia.

Weather tolerance: Plants of the new Petunia have been observed to be tolerant to rain and wind.

It is claimed:

1. A new and distinct cultivar of Petunia plant named 'Wespelila', as illustrated and described.

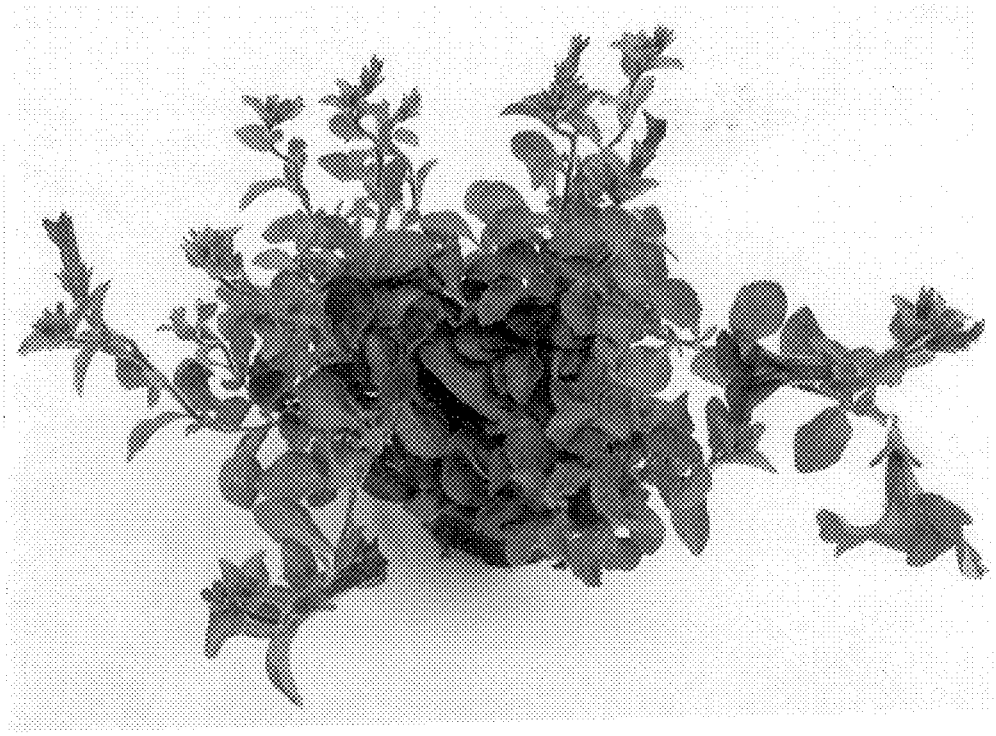
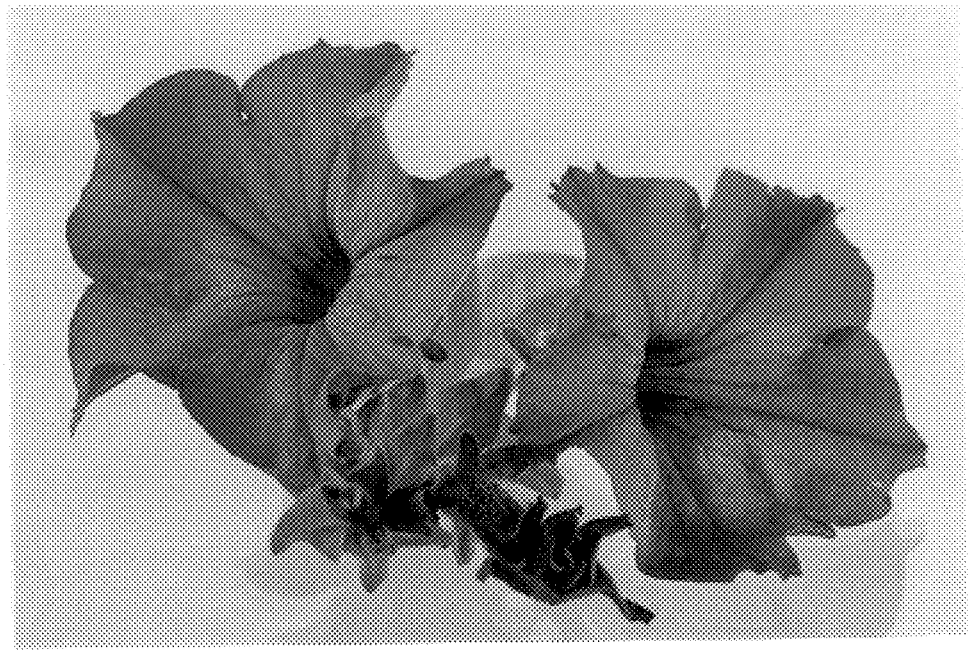

* * * * *